US00PP20334P2

(12) United States Plant Patent
Miedema-Jorna

(10) Patent No.: US PP20,334 P2
(45) Date of Patent: Sep. 22, 2009

(54) ***PETUNIA* PLANT NAMED 'FORT IMPROPURPLEPIC'**

(50) Latin Name: *Petunia×hybrida*
Varietal Denomination: Fort Impropurplepic

(75) Inventor: Anita Miedema-Jorna, De Lier (NL)

(73) Assignee: Fides B.V., De Lier (NL)

( * ) Notice: Subject to any disclaimer, the term of this patent is extended or adjusted under 35 U.S.C. 154(b) by 0 days.

(21) Appl. No.: 12/220,697

(22) Filed: Jul. 25, 2008

(51) Int. Cl.
*A01H 5/00* (2006.01)

(52) U.S. Cl. ..... Plt./356

(58) Field of Classification Search ..... Plt./356
See application file for complete search history.

*Primary Examiner*—Annette H Para
(74) *Attorney, Agent, or Firm*—C. A. Whealy

(57) ABSTRACT

A new and distinct cultivar of *Petunia* plant named 'Fort Impropurplepic', characterized by its upright to outwardly spreading and mounded growth habit; freely branching habit; freely flowering habit; large dark violet-colored flowers with white-colored margins; and good garden performance.

1 Drawing Sheet

Botanical designation: *Petunia×hybrida.*
Cultivar denomination: 'Fort Impropurplepic'.

BACKGROUND OF THE INVENTION

The present invention relates to a new and distinct cultivar of *Petunia,* botanically known as *Petunia×hybrida* and hereinafter referred to by the name 'Fort Inpropurplepic'.

The new *Petunia* is a product of a planned breeding program conducted by the Inventor in De Lier, The Netherlands. The objective of the breeding program is to create new freely-branching *Petunia* cultivars with early and freely flowering habit, and unique and attractive flower color.

The new *Petunia* originated from a cross-pollination made by the Inventor in 2006 in De Lier, The Netherlands of two unnamed proprietary seedling selections of *Petunia× hybrida,* not patented. The new *Petunia* was discovered and selected by the Inventor as a single flowering plant within the progeny of the stated cross-pollination in a controlled greenhouse environment in De Lier, The Netherlands in 2006.

Asexual reproduction of the new *Petunia* by terminal cuttings in a controlled greenhouse environment in De Lier, The Netherlands since 2007, has shown that the unique features of this new *Petunia* are stable and reproduced true to type in successive generations.

SUMMARY OF THE INVENTION

Plants of the new *Petunia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Fort Impropurplepic'. These characteristics in combination distinguish 'Fort Impropurplepic' as a new and distinct cultivar of *Petunia:*

1. Upright to outwardly spreading and mounded growth habit.
2. Freely branching habit.

3. Freely flowering habit.
4. Large dark violet-colored flowers with white-colored margins.
5. Good garden performance.

Plants of the new *Petunia* can be compared to plants of the female parent selection. Plants of the new *Petunia* differ from plants of the female parent selection in the following characteristics:

1. Plants of the new *Petunia* are more outwardly spreading and mounding than and not as upright as plants of the female parent selection.
2. Plants of the new *Petunia* and the female parent selection differ in flower color as plants of the female parent selection have darker-colored flowers.

Plants of the new *Petunia* can be compared to plants of the male parent selection. Plants of the new *Petunia* differ primarily from plants of the male parent selection in plant habit as plants of the new *Petunia* are more outwardly spreading and mounding than and not as upright as plants of the male parent selection.

Plants of the new *Petunia* can be compared to plants of *Petunia×hybrida* 'Viva Burgundy Picotee', not patented. In side-by-side comparisons conducted in De Lier, The Netherlands, plants of the new *Petunia* differed from plants of 'Viva Burgundy Picotee' primarily in flower color as flowers of plants of 'Viva Burgundy Picotee' had a smaller and less pronounced white-colored margin.

BRIEF DESCRIPTION OF THE PHOTOGRAPH

The accompanying colored photograph illustrates the overall appearance of the new *Petunia,* showing the colors as true as it is reasonably possible to obtain in colored reproductions of this type. Colors in the photograph may differ slightly from the color values cited in the detailed botanical description which accurately describe the colors of the new *Petunia.* The photograph comprises a side perspective view of a typical flowering plant of 'Fort Impropurplepic' grown in a container.

DETAILED BOTANICAL DESCRIPTION

The aforementioned photograph and following observations, measurements and values describe plants grown in De Lier, The Netherlands, under commercial practice during the spring and early summer in a glass-covered greenhouse with day and night temperatures averaging 18° C. Rooted young plants had been growing for twelve weeks when the photograph and description were taken. Plants used for the description were grown in 10.5-cm containers. In the following description, color references are made to The Royal Horticultural Society Colour Chart, 2001 Edition, except where general terms of ordinary dictionary significance are used.

Botanical classification: *Petunia×hybrida* 'Fort Impropurplepic'.

Parentage:

*Female, or seed, parent.*—Unnamed proprietary seedling selection of *Petunia×hybrida,* not patented.

*Male, or pollen, parent.*—Unnamed proprietary seedling selection of *Petunia×hybrida,* not patented.

Propagation:

*Type.* —By terminal cuttings.

*Time to initiate roots, summer.*—About five to seven days at temperatures of 19° C. to 20° C.

*Time to initiate roots, winter.*—About six to eight days at temperatures of 19° C. to 20° C.

*Time to produce a rooted young plant, summer.*—About 14 to 19 days at temperatures of 19° C. to 20° C.

*Time to produce a rooted young plant, winter.*—About two to three weeks at temperatures of 19° C. to 20° C.

*Rooting description.*—Fine; white in color.

*Rooting habit.*—Freely branching; moderately dense.

Plant description:

*Plant and growth habit.*—Upright to outwardly spreading and mounding growth habit. Freely branching habit with about six primary lateral branches each with multiple secondary lateral branches; pinching is typically not required. Moderately vigorous growth habit.

*Plant height.*—About 12 cm.

*Plant diameter.*—About 32 cm.

Lateral branch description:

*Length.*—About 19 cm.

*Diameter.*—About 3 mm.

*Internode length.*—About 1 mm to 1.5 mm.

*Strength.*—Moderately strong.

*Aspect.*—Initially upright to outwardly spreading.

*Texture.*—Densely pubescent; viscid.

*Color.*—Close to 143A.

Leaf description:

*Arrangement.*—Alternate, simple; sessile.

*Length.*—About 5 cm.

*Width.*—About 2.5 cm.

*Shape.*—Ovate.

*Apex.*—Acute.

*Base.*—Attenuate.

*Margin.*—Entire.

*Texture, upper and lower surfaces.*—Densely pubescent; viscid.

*Venation pattern.*—Pinnate; arcuate.

*Color.*—Developing and fully expanded leaves, upper surface: Close to 138A; venation, close to 144B. Developing and fully expanded leaves, lower surface: Close to 138B; venation, darker than 138B.

Flower description:

*Flower arrangement and habit.*—Relatively large salverform flowers arranged singly arising from leaf axils. Freely flowering habit with usually about 60 flowers developing per plant. Flowers not persistent. Flowers face upright to outwardly.

*Fragrance.*—None detected.

*Natural flowering season.*—Plants flower continuously from spring into the autumn in The Netherlands. Plants typically beginning flowering about 6.5 weeks after planting.

*Flower longevity.*—Individual flowers last about five days on the plant. Flowers persistent.

*Flower diameter.*—About 6.5 cm.

*Flower length (height).*—About 5 cm.

*Throat diameter.*—About 1.4 cm.

*Tube length.*—About 3.4 cm.

*Tube diameter, base.*—About 4 mm.

*Flower bud.*—Shape: Narrowly oblanceolate. Length: About 3.3 cm. Diameter: About 5 mm. Color: Close to 144B overlain with close to 83A.

*Corolla.*—Arrangement: Five petals fused at the base and opening into a flared trumpet. Petal length from throat: About 5.5 cm. Petal lobe width: About 3 cm. Petal shape: Spatulate. Petal apex: Retuse. Petal margin: Entire. Petal lobe texture, upper and lower surfaces: Smooth, glabrous; satiny. Throat texture: Smooth, glabrous. Tube texture: Densely pubescent. Color: Petal, when opening and fully opened, upper surface: Close to 83A; towards the margin, close to N155D; venation, similar to lamina. Petal, when opening and fully opened, lower surface: Close to 85B; venation, close to 144A or 83B. Throat: Close to 83A; venation, close to 83A. Tube: Close to 85B; venation, close to 144A or 83B.

*Calyx.*—Arrangement: One star-shaped calyx tube with five sepals fused at the base per flower. Sepal length: About 2 cm. Sepal width: About 4 mm. Sepal shape: Narrowly oblong. Sepal apex: Acute. Sepal base: Cuneate. Sepal margin: Entire. Sepal texture, upper and lower surfaces: Densely pubescent; viscid. Color, immature and mature, upper surface: Close to 138A. Color, immature and mature, lower surface: Close to 138B.

*Peduncles.*—Length: About 2.7 cm. Diameter: About 3 mm. Angle: Erect to about 40° from stem axis. Strength: Moderately strong. Texture: Densely pubescent; viscid. Color: Close to 144B.

*Reproductive organs.*—Stamens: Quantity per flower: Five. Filament length: About 2.1 cm. Filament color: Close to N155C. Anther shape: Broadly reniform. Anther length: About 2 mm. Anther color: Close to 155A. Pollen amount: Moderate. Pollen color: Close to 158A. Pistils: Quantity per flower: One. Pistil length: About 3 cm. Style length: About 2.2 cm. Style color: Close to 145C. Stigma shape: Flattened, three-lobed. Stigma color: Close to 145A. Ovary color: Close to 144C.

*Fruits/seeds.*—Fruit and seed development have not been observed on plants of the new *Petunia.*

Garden performance: Plants of the new *Petunia* have been observed to have good garden performance and tolerate wind, rain and temperatures ranging from about 5° C. to about 35° C.

Pathogen/pest resistance: Plants of the new *Petunia* have not been observed to be resistant to pathogens and pests common to *Petunia.*

It is claimed:

1. A new and distinct *Petunia* plant named 'Fort Impropurplepic' as illustrated and described.

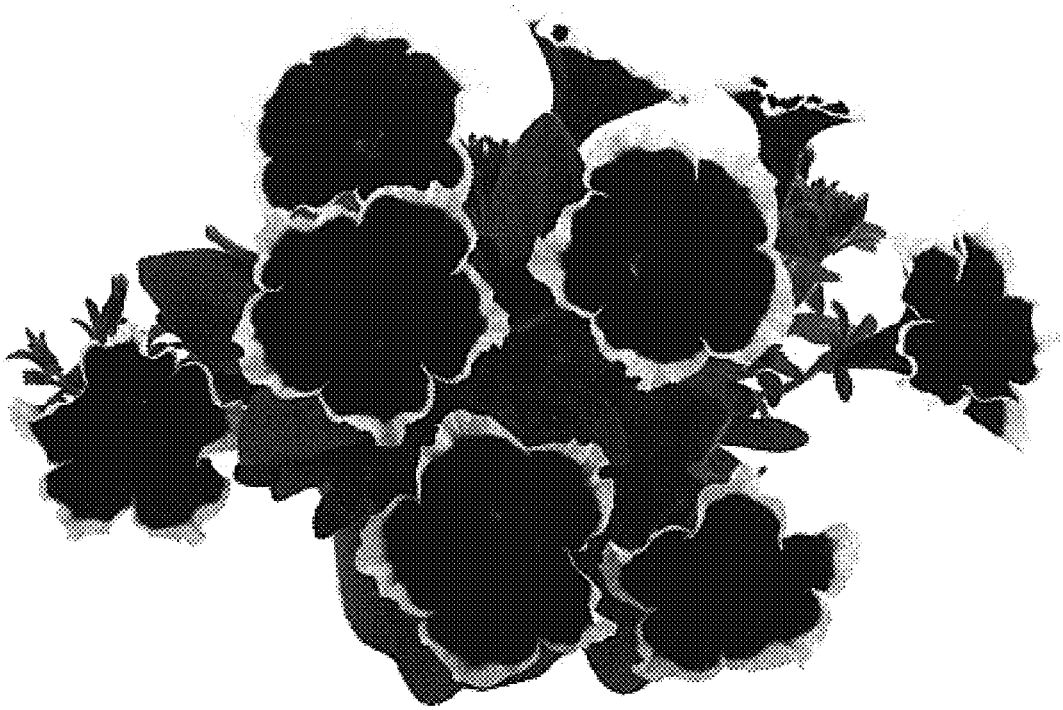

* * * * *